(12) United States Patent
Maletinska et al.

(10) Patent No.: US 10,751,390 B2
(45) Date of Patent: Aug. 25, 2020

(54) LIPIDATED PEPTIDES AS NEUROPROTECTIVE AGENTS

(71) Applicant: USTAV ORGANICKE CHEMIE A BIOCHEMIE AV CR, V.V.I., Prague (CZ)

(72) Inventors: Lenka Maletinska, Prague (CZ); Blanka Zelezna, Prague (CZ); Miroslava Blechova, Prague (CZ); Andrea Spolcova, Ceske Budejovice (CZ); Barbora Mikulaskova, Mnisek pod Brdy (CZ); Jaroslav Kunes, Prague (CZ); Stepan Strnad, Vlacice (CZ)

(73) Assignee: USTAV ORGANICKE CHEMIE A BIOCHEMIE AV CR, V.V.I., Prague (CZ)

( * ) Notice: Subject to any disclaimer, the term of this patent is extended or adjusted under 35 U.S.C. 154(b) by 0 days.

(21) Appl. No.: 16/550,654

(22) Filed: Aug. 26, 2019

(65) Prior Publication Data
US 2020/0016240 A1 Jan. 16, 2020

Related U.S. Application Data

(63) Continuation-in-part of application No. 15/307,262, filed as application No. PCT/CZ2015/000047 on May 20, 2015, now abandoned.

(30) Foreign Application Priority Data

May 27, 2014 (CS) ..................... 2014-364

(51) Int. Cl.
A61K 38/22 (2006.01)
A61P 25/28 (2006.01)

(52) U.S. Cl.
CPC ............. A61K 38/22 (2013.01); A61P 25/28 (2018.01)

(58) Field of Classification Search
None
See application file for complete search history.

(56) References Cited

U.S. PATENT DOCUMENTS

2016/0228563 A1 8/2016 Maletinska

FOREIGN PATENT DOCUMENTS

| WO | 2009033668 A2 | 3/2009 |
| WO | 2012176172 A2 | 12/2012 |
| WO | 2014009808 A2 | 1/2014 |

OTHER PUBLICATIONS

Merck Manual (<https://www.merckmanuals.com/professional/neurologic-disorders/movement-and-cerebellar-disorders/parkinson-disease> Jan. 5, 2020).*
Merck Manual (<https://www.merckmanuals.com/professional/neurologic-disorders/delirium-and-dementia/alzheimer-disease> Jan. 6, 2019).*
Tetsuya Tachibana et al: "Central administration of prolactin-releasing peptide shifts the utilities of metabolic fuels from carbohydrate to lipids in chicks", Physiology & Behavior, vol. 120, Aug. 1, 2013 (Aug. 1, 2013), pp. 40-45.
Yuki Takayanagi et al: "Endogenous prolactin-releasing peptide regulates food intake in rodents", Journal of Clinical Investigation, vol. 118, No. 12, Dec. 1, 2008 (Dec. 1, 2008), pp. 4014-4024.
White MF: "IRS2 integrates insulin/IGFI signalling with metabolism, neurodegeneration and longevity", Diabetes, Obesity and Metabolism 2014 Blackwell Publishing Ltd GBR, vol. 16, no. Supplementl, 2014, pp. 4-15.
Lenka Maletnsk et al: "Biological properties of prolactin-releasing peptide analogs with a modified aromatic ring of a C-terminal phenylalanine amide", Peptides, Elsevier, Amsterdam, NL, vol. 32, No. 9,Aug. 11, 2011 (Aug. 11, 2011), pp. 1887-1892.
Robert G Boyle et al: "Structure-activity studies on prolactin-releasing peptide (PrRP). Analogues of PrRP-(19-31)-peptide", Journal of Peptide Science, vol. 11, No. 3, Mar. 1, 2005 (Mar. 1, 2005), pp. 161-165.
Spolcova Andrea et al, "Anorexigenic lipopeptides ameliorate central insulin signaling and attenuate tau phosphorylation in hippocampi of mice with monosodium glutamate-induced obesity.", Journal of Alzheimer's Disease: JAD 2015, vol. 45, No. 3, 2015, pp. 823-835.
Merck Manual (https://www.merckmanuals.com/professional/neurologic-disorders/ peripheral-nervous-system-and-motor-unit-disorders/amyotrophic-lateral-sclerosis-als-and-other-motor-neuron-diseases-mnds)( accessed Oct. 25, 2018).
Merck Manual; Spinal muscular atrophy (neurodegenerative diseases) (https://www.merckmanuals.com/professional/neurologic-disorders/peripheral-nervous-system-and-motor-unit-disorders/spinal-muscular-atrophies-smas) (accessed Oct. 25, 2018).
Banks, William A., National Institute of Health, Drug Delivery to the Brain in Alzheimer's Disease: Consideration of the Blood-brain Barrier, (Adv Drug Deliv Rev. 2012;64(7):629-639), May 15, 2012.
International Search Report and Written Opinion for corresponding PCT application No. PCT/CZ2015/000047, dated Sep. 14, 2015.

* cited by examiner

*Primary Examiner* — James H Alstrum-Acevedo
*Assistant Examiner* — Tara L Martinez
(74) *Attorney, Agent, or Firm* — Notaro, Michalos & Zaccaria P.C.

(57) ABSTRACT

Lipidated neuropeptides PrRP31, PrRP20, containing C14 to C16 fatty acid, and their analogs, wherein a sequence of IRPVGRF-NH$_2$ at the C-terminus is variable in the site of isoleucine, valine and phenylalanine; said fatty acid is bound in position 1 or 11 for PrRP31 or its analog and in position 1 or 7 for PrRP20 or its analog; the bond comprises an amide bond between an amino acid having at least one free NH$_2$ group and a carboxylic group of the fatty acid and alternatively includes also a binding through arm $X^2$, which is a hydrophilic linker selected from a group comprising β-alanine, γ-aminobutyric acid or γ-glutamic acid; for use in the treatment and prevention of diseases, which are Alzheimer's disease (AD), Parkinson's disease (PD), cognitive impairment no dementia (CIND), brain trauma, and neurodegenerative changes and disorders.

1 Claim, 7 Drawing Sheets
Specification includes a Sequence Listing.

SEQUENCE LISTING

<160> NUMBER OF SEQ ID NOS: 11

<210> SEQ ID NO 1
<211> LENGTH: 7
<212> TYPE: PRT
<213> ORGANISM: Homo sapiens

<400> SEQUENCE: 1

Ile Arg Pro Val Gly Arg Phe
1               5

<210> SEQ ID NO 2
<211> LENGTH: 31
<212> TYPE: PRT
<213> ORGANISM: Homo sapiens

<400> SEQUENCE: 2

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 3
<211> LENGTH: 31
<212> TYPE: PRT
<213> ORGANISM: Rattus sp.

<400> SEQUENCE: 3

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 4
<211> LENGTH: 20
<212> TYPE: PRT
<213> ORGANISM: Homo sapiens

<400> SEQUENCE: 4

Thr Pro Asp Ile Asn Pro Ala Trp Tyr Ala Ser Arg Gly Ile Arg Pro
1               5                   10                  15

Val Gly Arg Phe
            20

<210> SEQ ID NO 5
<211> LENGTH: 20

```
<212> TYPE: PRT
<213> ORGANISM: Rattus sp.

<400> SEQUENCE: 5

Thr Pro Asp Ile Asn Pro Ala Trp Tyr Thr Gly Arg Gly Ile Arg Pro
1               5                   10                  15

Val Gly Arg Phe
            20

<210> SEQ ID NO 6
<211> LENGTH: 31
<212> TYPE: PRT
<213> ORGANISM: Artificial
<220> FEATURE:
<223> OTHER INFORMATION: PrRP31 analog

<400> SEQUENCE: 6

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 7
<211> LENGTH: 20
<212> TYPE: PRT
<213> ORGANISM: Artificial
<220> FEATURE:
<223> OTHER INFORMATION: PrRP20 analog

<400> SEQUENCE: 7

Thr Pro Asp Ile Asn Pro Lys Trp Tyr Ala Ser Arg Gly Ile Arg Pro
1               5                   10                  15

Val Gly Arg Phe
            20

<210> SEQ ID NO 8
<211> LENGTH: 31
<212> TYPE: PRT
<213> ORGANISM: Artificial
<220> FEATURE:
<223> OTHER INFORMATION: PrRP31 analog

<400> SEQUENCE: 8

Ser Arg Thr His Arg His Ser Met Glu Ile Lys Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 9
<211> LENGTH: 20
<212> TYPE: PRT
<213> ORGANISM: Artificial
<220> FEATURE:
<223> OTHER INFORMATION: PrRP20 analog

<400> SEQUENCE: 9

Thr Pro Asp Ile Asn Pro Lys Trp Tyr Ala Ser Arg Gly Ile Arg Pro
1               5                   10                  15

Val Gly Arg Phe
            20

<210> SEQ ID NO 10
<211> LENGTH: 31
<212> TYPE: PRT
```

```
<213> ORGANISM: Artificial
<220> FEATURE:
<223> OTHER INFORMATION: PrRP31 analog

<400> SEQUENCE: 10

Ser Arg Thr His Arg His Ser Met Glu Ile Lys Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 11
<211> LENGTH: 20
<212> TYPE: PRT
<213> ORGANISM: Artificial
<220> FEATURE:
<223> OTHER INFORMATION: PrRP20 analog

<400> SEQUENCE: 11

Thr Pro Asp Ile Asn Pro Lys Trp Tyr Ala Ser Arg Gly Ile Arg Pro
1               5                   10                  15

Val Gly Arg Phe
            20
```

LIPIDATED PEPTIDES AS NEUROPROTECTIVE AGENTS

CROSS-REFERENCED TO RELATED APPLICATIONS

This is a continuation in part application to the U.S. patent application Ser. No. 15/307,262, filed Oct. 27, 2016, which claims priority on international application No. PCT/CZ2015/000047 filed on May 20, 2015, and which also claims priority on Czech Republic patent application No. PV 2014-364 filed on May 27, 2014. The entire content of all these earlier applications is incorporated herein by explicit reference for all intents and purposes.

FIELD OF THE INVENTION

New analogs of prolactin releasing peptide represent neuroprotective agents for peripheral treatment and prevention of diseases and conditions which are Alzheimer's disease (AD), Parkinson's disease (PD), cognitive impairment no dementia (CIND) and brain trauma.

BACKGROUND OF THE INVENTION

AD is a serious neurodegenerative brain disease affecting mainly older people. The disease starts to manifest with memory decline, learning disorders, behavioral changes, impairment in orientation in time and space, loss of autonomic functions, finally results in complete dementia. The death comes on average 9 years after diagnosis.

Histopathologically, AD is characterized by two hallmarks in brain: intracelullar neurofibrilary tangles formed by hyperphosphorylated Tau protein and extracellular senile plaques of beta peptide.

Prolactin releasing peptide (PrRP) was discovered at the end of $20^{th}$ century. Naturally two isoforms of PrRP can be found in organism: peptide containing 31 amino acids (PrRP/1-31/; PrRP31) or 20 amino acids (PrRP/12-31/; PrRP20), its amino acid composition also exhibits small differences in various species (human, rat, bovine) (Hinuma et al., 1998).

PrRP is produced in neurons of many brain regions, mainly in medulla oblongata (in nucleus tractus solitarius and ventrolateral reticular nucleus), and hypothalamus (in paraventricular and dorsomedial nuclei) (Maruyama et al., 1999; Lee et al., 2000), less in pituitary gland, and amygdala. In the periphery PrRP can be found in adrenal medulla, testis, pancreas, and small and large intestines.

PrRP receptor, GPR10, is extensively expressed in the whole brain; it can be found in anterior pituitary, amygdala, hypothalamus, brainstem, and medulla oblongata. In the periphery GPR10 can be found in adrenal medulla, and significantly increased expression was observed in human and rat pancreas.

Subsequently, new modified analogs of neuropeptides PrRP31 and PrRP20 were synthesized, with changes in amino acid chain, lipidated with fatty acid (e.g. myristoylated or palmitoylated) at the N-terminus, however, for use in regulating food intake (WO2014/009808) and regulating blood glucose levels (US 2016/228563).

Neuropeptides PrRP31 and PrRP20 and their analogs lipidated either at N-terminus or in the middle of their peptide chain showed higher affinity to endogenous GPR10 receptor also in in vitro experiments (WO2014/009808, US 2016/228563).

Lipidated neuropeptides based on PrRP20 and PrRP31 and their analogs and their activities are known also from WO 2009/033668; Tachibana T. et al: Physiology and Behavior, vol. 120, 2013, 40-45; Takayanagi Y. et al.: Journal of Clinical Investigation, vol. 118, 2008, 4014-4024.

Nowadays, drugs slowing the AD progression and improving cognitive functions are used. These are inhibitors of acetylcholinesterase, which increase acetylcholine concentration in the brain and inhibitors of N-methyl-D-aspartate receptors (e.g. memantin).

Because of the high incidence of insulin resistance in AD patients, it is not possible to use insulin as an AD treatment. It is hypothesized that agents increasing insulin sensitivity, such as metformim, insulin secretagogues such as glucagon-like peptide-1 (GLP-1), gastric-inhibitory peptide (GIP) and their analogs could act as AD treatment.

There is a need to provide further substances with neuroprotective effect which could be useful in the treatment of neurodegenerative diseases.

DISCLOSURE OF THE INVENTION

The present invention provides lipidated neuropeptides based on prolactin-releasing peptide (PrRP-based neuropeptides) selected from prolactin-releasing peptide 20 (PrRP20), prolactin-releasing peptide 31 (PrRP31) and their analogs, wherein in the C-terminal sequence IRPVGRF-$NH_2$ (SEQ ID NO. 1), one or more of isoleucine, valine and phenylalanine can be replaced by another amino acid; said PrRP-based neuropeptide containing C14 and/or C16 fatty acid chain, said fatty acid is bound in position 1 or 11 for PrRP31 or its analogs and in position 1 or 7 for PrRP20 or its analogs; said fatty acid being bound by a bond between an amino acid having at least one free $NH_2$, OH or SH group and the carboxylic group of the fatty acid or through a hydrophilic linker $X_2$ selected from the group comprising polyoxyethylene moiety, arylalkyl moiety, or a saturated or unsaturated, linear or branched $C_3$-$C_8$ hydrocarbon chain, wherein some carbon atoms may be replaced by heteroatoms selected from a group comprising N, S, and O; said chain carrying at least one and preferably two amino groups or carboxylic acid groups, one of which may be substituted to form a group selected from: $CONH_2$; NH-polyoxyethylene; $COOM_1$ wherein $M_1$ is alkali metal, preferably Na or K; CN; $COOR_1$, $COR_1$, or $CONHR_1$ wherein $R_1$ is selected from a group comprising lower alkyl, arylalkyl, polyoxyethylene, methylpolyoxyethylene, and aminoethylpolyoxyethylene; $(CHOH)_nR_2$ where $R_2$ is H or COOH and n is an integer from 2 to 10; or $(CH)_nN_+R_3$, wherein $R_3$ is the same or different, selected from H and $C_1$-$C_4$ alkyl; for use in a method of treatment and prevention of neurodegenerative diseases, such as Alzheimer's disease (AD), Parkinson's disease (PD), cognitive impairment no dementia (CIND) and brain trauma.

The PrRP31 and/or PrRP20 include variants found in various animal species. Preferred are the human and rat variants.

Preferably, in the sequence of the C-terminal heptapeptide as mentioned above, izoleucine can be replaced by phenylglycine or alanine, valine can be replaced by phenylglycine and/or terminal phenylalanine can be replaced by dichlorophenylalanine, pentafluorophenylalanine, nitrophenylalanine, histidine, benzylhistidine, naphthylalanine, tryptofane, pyroglutamic acid, benzylcysteine, benzyl-O-glutamate, tetrachlorophenylalanine, methyl-O-phenylalanine or methyl-NH-phenylalanine.

The binding of the fatty acid thus includes either a direct bond between an amino acid of the PrRP chain having at least one free amino, SH or OH group and the carboxylic group of the fatty acid, or a bond through $X_2$, wherein $X_2$ is a hydrophilic linker selected from a group comprising polyoxyethylene moiety, arylalkyl moiety, or a saturated or unsaturated, linear or branched $C_3$-$C_8$ hydrocarbon chain, wherein some carbon atoms may be replaced by heteroatoms selected from a group comprising N, S, and O; said chain carrying at least one and preferably two amino groups or carboxylic acid groups, one of which may be substituted to form a group selected from: $CONH_2$; NH-polyoxyethylene; $COOM_1$ wherein $M_1$ is alkali metal, preferably Na or K; CN; $COOR_1$, $COR_1$, or $CONHR_1$ wherein $R_1$ is selected from a group comprising lower alkyl, arylalkyl, polyoxyethylene, methylpolyoxyethylene, and aminoethylpolyoxyethylene; $(CHOH)_nR_2$ wherein $R_2$ is H or COOH and n is an integer from 2 to 10; or $(CH)_nN_+R_3$, where $R_3$ is the same or different, selected from H and $C_1$-$C_4$ alkyl.

Preferably, $X_2$ is a hydrophilic linker selected from the group comprising β-alanine, γ-aminobutyric acid and γ-glutamic acid.

When the fatty acid is bound in position 11 for PrRP31 or its analogs, the PrRP or its analogs have an amino acid having a free $NH_2$, OH or SH group in position 11, and when the fatty acid is bound in position 7 for PrRP20 or its analogs, the PrRP20 or its analogs have an amino acids having a free $NH_2$, OH or SH group in position 7. Amino acids having a free $NH_2$, OH or SH group include, for example, lysine, arginine, serine, cysteine, tyrosine.

The present invention provides, more particularly, the lipidated analogs of PrRP20 or PrRP31 (rat and human) according to the formulae:

(X)SRTHRHSMEIRTPDINPAWYASRGIRPVGRF-NH$_2$ (1), (SEQ ID NO. 2)

(X)SRAHQHSMETRTPDINPAWYTGRGIRPVGRF-NH$_2$ (2), (SEQ ID NO. 3)
or (X)TPDINPAWYASRGIRPVGRF-NH$_2$ (3), (SEQ ID NO. 4)

(X)TPDINPAWYTGRGIRPVGRF-NH$_2$ (4), (SEQ ID NO. 5)

wherein X=$X_1$ or $X_1X_2$; $X_1$ being tetradecanoic or hexadecanoic acid, which is bound in a position 1 to an amino acid of the above mentioned peptide chain either directly or through $X_2$, $X_2$ being a hydrophilic linker selected from the group consisting of β-alanine, γ-amino butyric acid and γ-glutamic acid, and wherein in the C-terminal sequence IRPVGRF-NH$_2$, one or more of isoleucine, valine and phenylalanine can be replaced by another amino acid;

for use in the treatment and prevention, preferably by peripheral administration, of neurodegenerative diseases, which are Alzheimer's disease (AD), Parkinson's disease (PD), cognitive impairment no dementia (CIND) and brain trauma.

In a preferred embodiment, the lipidated analogs of PrRP20 or PrRP31 according to the formulae:

(N-palm)SRTHRHSMEIRTPDINPAWYASRGIRPVGRF-NH$_2$ (5) (SEQ ID NO. 6)
and (palm)TPDINPKWYASRGIRPVGRF-NH$_2$ (6); (SEQ ID NO. 7)

wherein palm is hexadecanoic acid, and
wherein in the C-terminal sequence IRPVGRF-NH$_2$, one or more of isoleucine, valine and phenylalanine can be replaced by another amino acid;
are provided for use in the treatment and prevention, by peripheral administration, of neurodegenerative diseases, which are Alzheimer's disease (AD), Parkinson's disease (PD), cognitive impairment no dementia (CIND), brain trauma, and neurodegenerative changes and disorders.

In another embodiment, the lipidated analogs of PrRP20 or PrRP31 according to the formulae:

SRTHRHSMEIK(palm)TPDINPAWYASRGIRPVGRF-NH$_2$ (7), (SEQ ID NO. 8)

TPDINPK(palm)WYASRGIRPVGRF-NH$_2$ (8), (SEQ ID NO. 9)

SRTHRHSMEIKTPDINPAWYASRGIRPVGRF-NH$_2$ (9), and (SEQ ID NO. 10)
       |
     $X^2$(palm)

TPDINPKWYASRGIRPVGRF-NH$_2$ (10); (SEQ ID NO. 11)
  |
$X^2$(palm)

wherein palm is hexadecanoic acid and $X^2$ is γ-glutamic acid,
wherein in the C-terminal sequence IRPVGRF-NH$_2$, one or more of isoleucine, valine and phenylalanine can be replaced by another amino acid;
are provided for use in the treatment and prevention, by peripheral administration, of neurodegenerative diseases, which are Alzheimer's disease (AD), Parkinson's disease (PD), cognitive impairment no dementia (CIND), brain trauma.

A further embodiment of the invention relates to the use of lipidated neuropeptides based on prolactin-releasing peptide (PrRP based neuropeptides) selected from prolactin-releasing peptide 20 (PrRP20), prolactin-releasing peptide 31 (PrRP31) and their analogs, wherein in the C-terminal sequence IRPVGRF-NH$_2$ (SEQ ID NO. 1), one or more of isoleucine, valine and phenylalanine can be replaced by another amino acid; said PrRP-based neuropeptide containing $C_{14}$ and/or $C_{16}$ fatty acid chain, said fatty acid is bound in position 1 or 11 for PrRP31 or its analogs and in position 1 or 7 for PrRP20 or its analogs; said fatty acid being bound by a bond between an amino acid having at least one free $NH_2$, OH or SH group and the carboxylic group of the fatty acid or through a hydrophilic linker $X_2$ selected from the group comprising polyoxyethylene moiety, arylalkyl moiety, or a saturated or unsaturated, linear or branched $C_3$-$C_8$ hydrocarbon chain, wherein some carbon atoms may be replaced by heteroatoms selected from a group comprising N, S, and O; said chain carrying at least one and preferably two amino groups or carboxylic acid groups, one of which may be substituted to form a group selected from: $CONH_2$; NH-polyoxyethylene; $COOM_1$ wherein $M_1$ is alkali metal, preferably Na or K; CN; $COOR_1$, $COR_1$, or $CONHR_1$ wherein R₁ is selected from a group comprising lower alkyl, arylalkyl, polyoxyethylene, methylpolyoxyethylene, and aminoethylpolyoxyethylene; (CHOH)$_n$R₂ where R₂ is H or COOH and n is an integer from 2 to 10; or (CH)$_n$N⁺R₃, wherein R₃ is the same or different, selected from H and C₁-C₄ alkyl; and the PrRP31 or its analogs may have the amino acid in position 11 replaced by an amino acid having a free NH₂, OH or SH group, particularly when the fatty acis is bound in position 11 for PrRP31 or its analogs; and PrRP20 or its analogs may have the amino acid in position 7 replaced by an amino acid having a free NH₂, OH or SH group, particularly when the fatty acid is bound in position 7 for PrRP20 or its analogs; for the manufacture of a medicament for treatment and prevention, by peripheral administration, of neurodegenerative diseases, which are Alzheimer's disease (AD), Parkinson's disease (PD), cognitive impairment no dementia (CIND) and brain trauma.

Another embodiment of the invention provides a method of treatment and prevention of neurodegenerative diseases, which are Alzheimer's disease (AD), Parkinson's disease (PD), cognitive impairment no dementia (CIND) and brain trauma, comprising a step of administering to a subject of need of such treatment or prevention, preferably by peripheral administartion, lipidated neuropeptides based on prolacting-releasing peptide (PrRP based neuropeptides) selected from prolactin-releasing peptide 20 (PrRP20), prolactin-releasing peptide 31 (PrRP31) and their analogs, wherein in the C-terminal sequence IRPVGRF-NH₂ (SEQ ID NO. 1), one or more of isoleucine, valine and phenylalanine can be replaced by another amino acid; said PrRP-based neuropeptide containing C14 and/or C16 fatty acid chain, said fatty acid is bound in position 1 or 11 for PrRP31 or its analogs and in position 1 or 7 for PrRP20 or its analogs; said fatty acid being bound by a bond between an amino acid having at least one free NH₂, OH or SH group and the carboxylic group of the fatty acid or through a hydrophilic linker X₂ selected from the group comprising polyoxyethylene moiety, arylalkyl moiety, or a saturated or unsaturated, linear or branched C₃-C₈ hydrocarbon chain, wherein some carbon atoms may be replaced by heteroatoms selected from a group comprising N, S, and O; said chain carrying at least one and preferably two amino groups or carboxylic acid groups, one of which may be substituted to form a group selected from: CONH₂; NH-polyoxyethylene; COOM₁ wherein M₁ is alkali metal, preferably Na or K; CN; COOR₁, COR₁, or CONHR₁ wherein R₁ is selected from a group comprising lower alkyl, arylalkyl, polyoxyethylene, methylpolyoxyethylene, and aminoethylpolyoxyethylene; (CHOH)$_n$R₂ where R₂ is H or COOH and n is an integer from 2 to 10; or (CH)$_n$N⁺R₃, wherein R₃ is the same or different, selected from H and C₁-C₄ alkyl;

and the PrRP31 or its analogs may have the amino acid in position 11 replaced by an amino acid having a free NH₂, OH or SH group, particularly when the fatty acis is bound in position 11 for PrRP31 or its analogs; and PrRP20 or its analogs may have the amino acid in position 7 replaced by an amino acid having a free NH₂, OH or SH group, particularly when the fatty acid is bound in position 7 for PrRP20 or its analogs.

Another embodiment of the invention provides a method of treatment and prevention of neurodegenerative diseases, which are Alzheimer's disease (AD), Parkinson's disease (PD) or cognitive impairment no dementia (CIND), comprising a step of administering to a subject of need of such treatment or prevention, preferably by peripheral administartion the lipidated analogs of PrRP20 or PrRP31 according to the formulae:

```
                                            (SEQ ID NO. 6)
(N-palm)SRTHRHSMEIRTPDINPAWYASRGIRPVGRF-NH₂ (5),
                                            (SEQ ID NO. 7)
(palm)TPDINPKWYASRGIRPVGRF-NH₂ (6),
                                            (SEQ ID NO. 10)
SRTHRHSMEIKTPDINPAWYASRGIRPVGRF-NH₂ (9), and
               |
             X²(palm)
                                            (SEQ ID NO. 11)
TPDINPKWYASRGIRPVGRF-NH₂ (10);
     |
   X²(palm)
``` wherein palm is hexadecanoic acid and X² is γ-glutamic acid.

EXAMPLES

Used Abbreviations

ANOVA—analysis of variance
ARC—nucleus arcuatus
GSK-3β-glycogen synthase kinase—30
MWM—Morris water maze
PDK-1—phosphoinositide-dependent kinase—1
SC—subcutaneous
SDS—sodium dodecyl sulfate
SEM—standard error of the mean
WB—Western blot
LiPR31—an analog of PrRP31 palmitoylated at $Lys^{11}$ through gamma glutamic acid linker
Tested Compounds According to the structure-activity studies, analogs of PrRP31 and PrRP20, rat (identical to mouse) or human, lipidated at N-terminal or amino acid containing amino group, using C14 or C16 fatty acid. Methionine in position 8 in PrRP31 was replaced by more stable norleucine. In Thy Tau22 mice study, an analog of PrRP31 palmitoylated at $Lys^{11}$ (Lys instead of Arg) through gamma glutamic acid linker (hereinafter referred to as LiPR31) was used.

Lipidated analogs of PrRP31 and PrRP20 were synthesized by solid-phase synthesis at the IOCB AS CR, Prague, on the peptide synthesis department, as described by Maixnerová et al. (Maletínská et al., 2007).

Liraglutide was purchased from Novo Nordisk A/S (Bagsvaerd, Denmark).

Animals

To examine neuroprotective properties, insulin resistant animal model was used, e.g. mouse model with obesity induced by MSG. These mice are characterized by growth hormone insufficiency, pituitary and optic nerves atrophy, and infertility (Olney, 1969). In their brains the reduced nucleus arcuatus, enlarged third brain ventricle, and narrowed eminentia mediana are observed. Total number of neurons in ARC is reduced about 75% in MSG mice compared to their controls; however, the number of neurons does not differ significantly in other brain regions (Elefteriou et al., 2003).

The imbalance between food intake and energy expenditure developed at MSG obese mice leads to hypophagia and an increased adipose tissue; compared to their control, MSG obese mice have even 8 times higher weight of white adipose tissue (Maletinski et al., 2006). They have also increased leptin and glucose blood concentration, and insulin resistance (Maletinski et al., 2006).

For evaluation of the the neuroprotecitve effect of palmitoylated PrRP LiPR31, the model of AD like pathology, Thy-Tau22 mice, was used. Thy-Tau22 mice overexpress human 4R-Tau protein with mutations G272V and P301S. These mice develop memory deficits, Tau hyper-phosphorylation at different epitopes, such as Ser202, Thr205, Thr212, Ser214, Thr231, Ser396, in CA1 region of hippocampus, and neurofibrillary tangles formation (Schindowski et al., 2006; Van der Jeugd et al., 2011).

MSG Mice

Male mice of strain NMRI (Harlan, Italy) were housed at the certified animal facility of IOCB AS CR, Prague, in the campus of Academy of Science in Krč at 22±2° C., they had free access to water and food They were fed standard chow diet St-1 (Mlyn Kocanda, Jesenice, Czech Republic), which contained 66% calories as carbohydrates, 25% as protein, and 9% as fat; its energy content was 3.4 kcal/g. Daily cycle was 12/12 hours, lights on at 6:00 a.m. All animal experiments followed the ethical guidelines for animal experiments and the Czech Republic Act No. 246/1992.

For obesity induction, the newborn NMRI mice were SC administered with sodium glutamic acid (Sigma, St. Louis, USA) at dose 4 mg/g of body weight at postnatal days 2-5. These MSG-obese mice were fed the same standard diet as the control group. The food and body weight were monitored once per week. For the study, MSG and control male mice at the age of 2 and 6 months were used.

6-Month-Old MSG Mice Treatment with Peptides Increasing Insulin Sensitivity

Groups of MSG mice (n=10 animals per group) were for 14 days SC administered with liraglutide at a dose 0.2 mg/kg, or palmitoylated analog of PrRP31 at a dose 5 mg/kg, or palmitoylated analog with PrRP31 with dichlorophenylalanin in position 31 at a dose 5 mg/kg dissolved in saline, twice a day, at 8 a.m. and 6:00 p.m. Control mice (n=10 animals per group), NMRI and MSG, were injected in the same manner with saline (the volume was always 0.2 ml/mouse).

Spatial Memory Testing at 6 Months Old MSG Mice

The spatial memory was tested using Morris water maze (MWM) following the protocol described in article of Vorheese and Williamse (Vorhees and Williams, 2006) in 6-month-old MSG mice and their age-matched controls.

Thy-Tau22 Mice

Thy-Tau22 female mice and their age-matched WT controls (C57Bl/6 origin) were a kind gift from INSERM laboratory, Lille, France, the research group "Alzheimer & Tauopathies". Mice were obtained at the age of 7 months, and were housed 3-4 per cage in the certified animal facility of the Institute of Physiology AS CR, Prague, Czech Republic, with free access to water and Altromin diet (Altromin, Eastern-Westphalia, Germany). Daily cycle was 12/12 hours, lights on at 6:00 a.m. All animal experiments followed the ethical guidelines for animal experiments and the Czech Republic Act No. 246/1992.

Thy-Tau22 Mice Treatment with LiPR31

Thy-Tau22 mice were infused for 2 months with LiPR31, with doses 5 mg/kg/day dissolved in PBS/5% Tween 80 pH 6, using SC Alzet® osmotic pumps. Control mice were infused with PBS/5% Tween 80. Alzet® osmotic pumps were subcutaneously (SC) implanted in short-term ether anesthesia, and were changed after one months of experiment.

Spatial Memory Testing of Thy-Tau22 Mice

The spatial memory was tested before the beginning of the treatment 5 with LiPR31, and after 2 months of the treatment, using the Y-maze. Experiment was performed following the protocol described by Belarbi et al. (Belarbi et al., 2011).

Tissue Dissection

Overnight (15 hours) fasted mice with ad libitum access to water were weighed, and their plasma glucose concentration was measured using Glucocard glucometer. After decapitation, the brains were dissected on ice, and cut between hemispheres. For immunohistochemical staining the half of the brain was fixed for 24 hours in 4% paraformaldehyde and dehydrated in 70% ethanol, afterward. For the western blot (WB) analysis, the hippocampus was dissected from the second half of the brain, and lysed in cold lysis buffer (62.5 mmol·l$^{-1}$ Tris-HCl, pH 6.8 with 1% sodium deoxycholate, 1% Triton X-100 Complete, 50 mmol·l$^{-1}$ NaF, 1 mmol·l$^{-1}$ Na$_3$VO$_4$), homogenized, sonicated 10 minutes and stored at −20° C. The blood plasma was prepared, and stored at −20° C.

Western Blot Analysis of Proteins Implicated in Insulin Signaling Cascade and Detection of Hyperphosphorylation of Tau Protein In homogenized hippocampi the protein level was measured using BCA kit (Pierce, Thermo Fisher Scientific, Rockfor, Ill., USA), then the samples were diluted in sample buffer (62.5 mmol/l Tris-HCl pH 6.8, 10% glycerol, 2% SDS, 0.01% bromfenol blue, 5% merkaptoethanol, 50 mmol/l NaF and 1 mmol/l Na$_3$VO$_4$) to final concentration 1 ug/l. WB method and analysis of the results were performed according Nagelová et al. (Nagelova et al., 2014). The list of the proteins detected as well as dilutions of used antibodies is shown in Table 1.

TABLE 1

| Antibody | Company | Dilution |
|---|---|---|
| Rabbit monoclonal antibody against Phospho-Akt (Ser473) | Cell Signaling Technology, Beverly, MA, USA | 1:1000 5% BSA TBS/tween-20 |
| Rabbit monoclonal antibody against Phospho -Akt (Thr308) | Cell Signaling Technology, Beverly, MA, USA | 1:1000 5% BSA TBS/tween-20 |
| Rabbit monoclonal antibody against total Akt | Cell Signaling Technology, Beverly, MA, USA | 1:1000 5% BSA TBS/tween-20 |
| Rabbit monoclonal antibody against Phospho -GSK-3β (Ser9) | Cell Signaling Technology, Beverly, MA, USA | 1:1000 5% BSA TBS/tween-20 |
| Rabbit monoclonal antibody against total GSK-3β | Cell Signaling Technology, Beverly, MA, USA | 1:1000 5% BSA TBS/tween-20 |
| Rabbit monoclonal antibody against Phospho -PDK1 (ser241) | Cell Signaling Technology, Beverly, MA, USA | 1:1000 5% BSA TBS/tween-20 |
| Rabbit monoclonal antibody against total PDK1 | Cell Signaling Technology, Beverly, MA, USA | 1:1000 5% BSA TBS/tween-20 |
| Rabbit polyclonal antibody against Tau [pS396] | Invitrogen Grand Island, NY, USA | 1:10 000 5% BSA TBS/tween-20 |
| Rabbit polyclonal antibody against Tau [pT231] | Invitrogen Grand Island, NY, USA | 1:1000 5% BSA TBS/tween-20 |
| Rabbit polyclonal antibody against Tau [pT212] | Invitrogen Grand Island, NY, USA | 1:1000 5% BSA TBS/tween-20 |
| Anti-total Tau CTer | Gift from Dr. M.-C. Galas, Inserm, Lille, Francie | 1:10 000 5% milk TBS/tween-20 |
| Mouse monoclonal antibody against Tau1 (Ser195, 198, 199, 202) | Millipore, Billerica, MA, USA | 1:10 000 5% milk TBS/tween-20 |
| Mouse monoclonal antibody against β-actin | Sigma, St. Louis, MO, USA | 1:10 000 5% milk TBS/tween-20 |

Immunohistochemical Staining of Hyperphosphorylated Tau Protein

To verify the results obtained from WB analysis the immunohistochemical staining was performed. Ten micrometer (10 μm) thick sections were prepared at INSERM, Lille, France. Immunohistochemical staining was performed according the method from Violet et al. (Violet et al., 2014).

Statistical Analysis

Statistical analysis was calculated by 1-way ANOVA, with Dunnett post-hoc test, or by Student t-test, using GrapPad software (San Diego, Calif., USA). Data are presented as mean±SEM.

Results:

MWM with 6-Month-Old MSG Obese Mice

Figure 1:
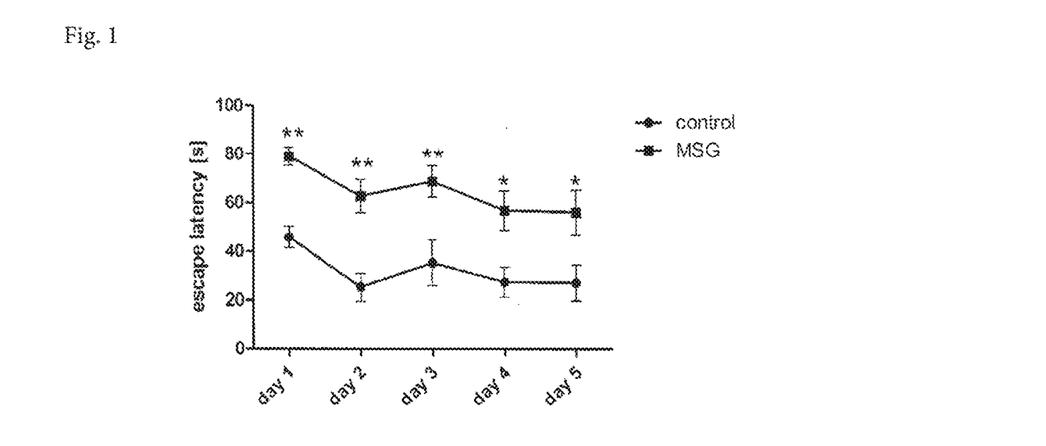
FIG. 1 shows the escape latency in Morris water maze test (MWM). The experiment was performed for 5 days, with 4 sessions per day, each session from different starting point, using MSG mice and their controls. Data are mean±SEM, n=10 mice per group. Statistical analysis is 2-way ANOVA with Bonferroni post hoc test. Significance is * P<0.05 and ** P<0.01.

The escape latency was measured in 6-month-old MSG mice and their age-matched controls. Experiment was performed 5 days with 4 sessions per day. As shown in FIG. 1, MSG mice had significantly increased escape latency compared to the control group.

Figure 2A:
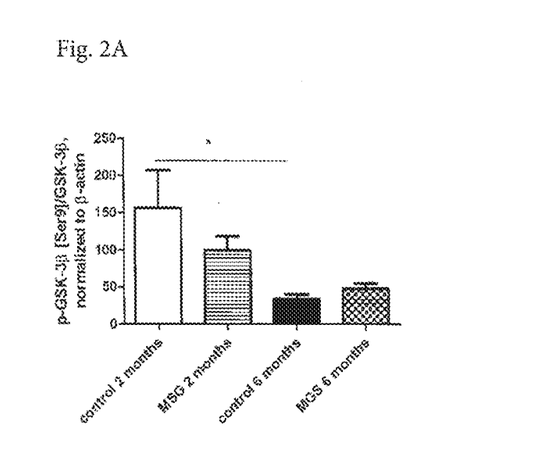
FIGS. 2A, 2B and 2C show phosphorylation of GSK-33 at Ser9 and Tau phosphorylation at Ser396 and Thr231 in the hippocampi of 2 and 6-month-old MSG mice and their age-matched controls. Phosphorylation in the hippocampus was determined using Western blot (WB). Data are mean±SEM, n=7-10 mice per group. Statistical analysis is 1-way ANOVA with Bonferroni post hoc test. Significance is * P<0.05 and *** P<0.001.
Figure 2B:
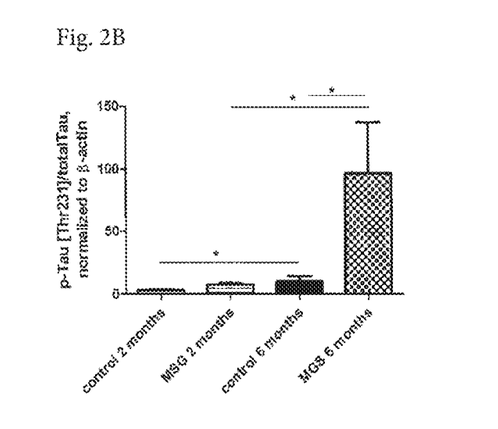
Figure 2C:
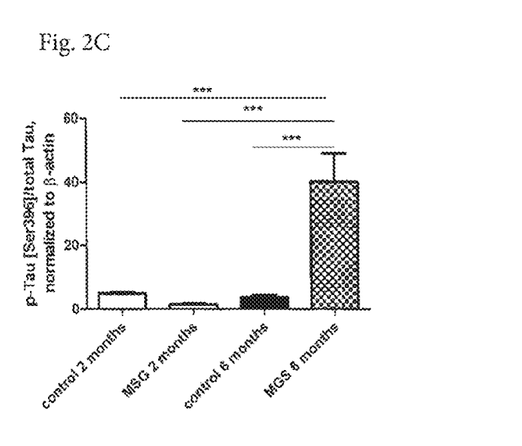
Figure 3A:
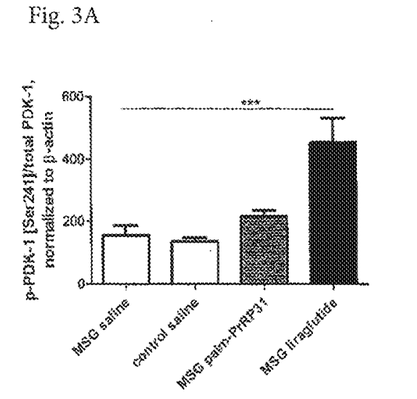
FIGS. 3A, 3B, 3C and 3D show phosphorylation of insulin signaling cascade in hippocampi of 6-month-old MSG mice after 14-day treatment with liraglutide and palmitoylated human PrRP31 (lipidated in position 1). Liraglutide (0.2 mg/kg) and palmitoylated human PrRP31 (5 mg/kg) were subcutaneously administered twice a day, in the morning and in the evening. Saline treated mice served as a control. Rate of phosphorylation was determined using WB. Data are mean±SEM, n=7-10 mice per group. Statistical analysis is 1-way ANOVA with Bonferroni post hoc test. Significance is * P<0.05 and *** P<0.001.
Figure 3B:
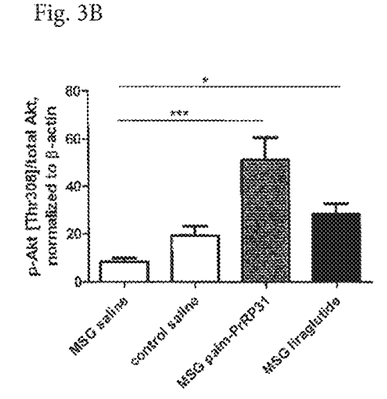
Figure 3C:
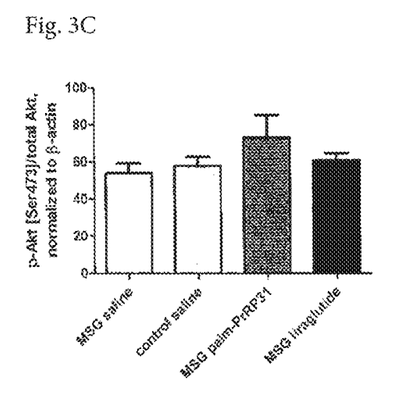
Figure 3D:
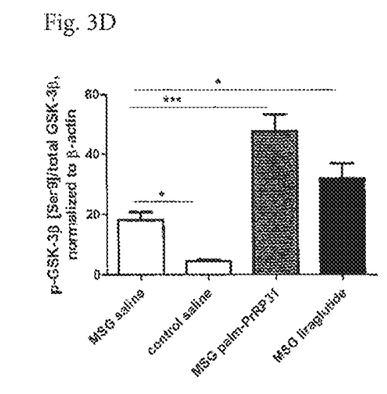

Insulin Signaling Activation and Tau Phosphorylation in Hippocampi of 2- and 6-Month-Old MSG Mice and their Controls Activation of insulin signaling cascade and Tau protein phosphorylation were measured by WB analysis in hippocampi of MSG obese mice and their controls aged 2 and 6 months. The phosphorylation of GSK-3β at Ser9 was detected. As shown in FIG. 2A, the phosphorylation was decreased in MSG mice at the age of 2 months, and furthermore significantly decreased with age of 6 months, compared to the control mice. A decreased phosphorylation of Ser9 at GSK-3β probably caused increased phosphorylation of Tau protein at epitopes Ser396 and Thr231, as shown in FIGS. 2B and 2C. The 6-month old MSG mice were proven as suitable model for testing the effect of insulin-sensitizing compounds.

Insulin Signaling Cascade in Hippocampi of 6-Month-Old MSG Mice after 14-Day

Treatment with Palmitoylated Analog of PrRP31 and Liraglutide Enhanced activation of kinases implicated in insulin signaling cascade was observed in hippocampi of 6-month-old MSG mice after 14-day intervention, either with palmitoylated analog of PrRP31, or with liraglutide, as shown in FIGS. 3A-3D. After liraglutide treatment, significantly increased phosphorylation was observed in PDK-1, Akt (Thr308), and GSK-33 (Ser9); more pronounced phosphorylation was observed in-Akt (Thr308), and GSK-3β (Ser9) after treatment with palmitoylated analog of PrRP31.

Figure 4A:
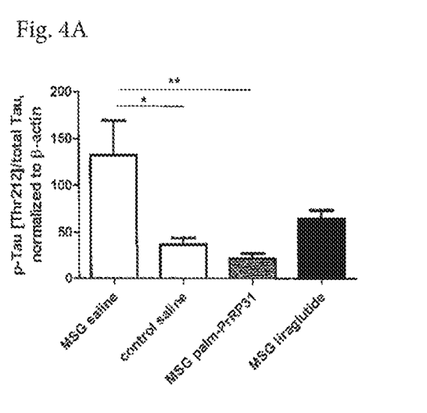
FIGS. 4A, 4B, 4C and 4D show phosphorylation at different epitopes of Tau protein in hippocampi of 6-month-old MSG mice after 14-day treatment with liraglutide and palmitoylated human PrRP31. Liraglutide (0.2 mg/kg) and palmitoylated human PrRP31 (5 mg/kg) were subcutaneously administered twice a day, in the morning and in the evening. Saline treated mice served as a control. Rate of phosphorylation was determined using WB. Data are mean±SEM, n=7-10 mice per group. Statistical analysis is 1-way ANOVA with Bonferroni post hoc test. Significance is * P<0.05 and *** P<0.001.
Figure 4B:
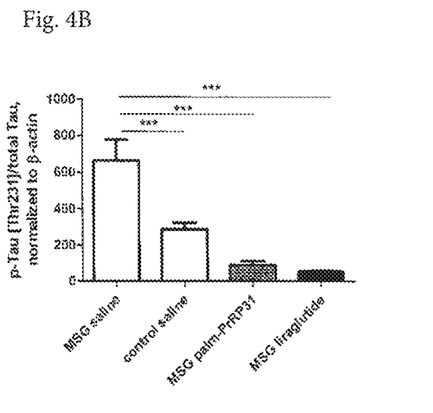
Figure 4C:
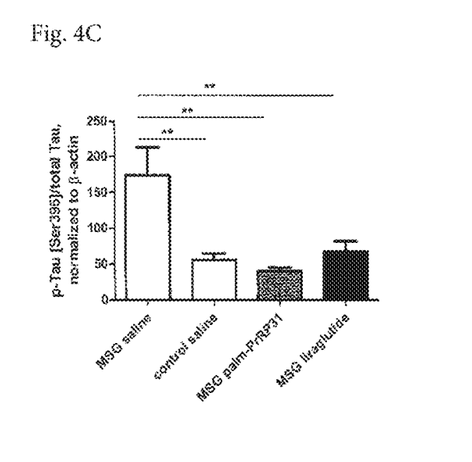
Figure 4D:
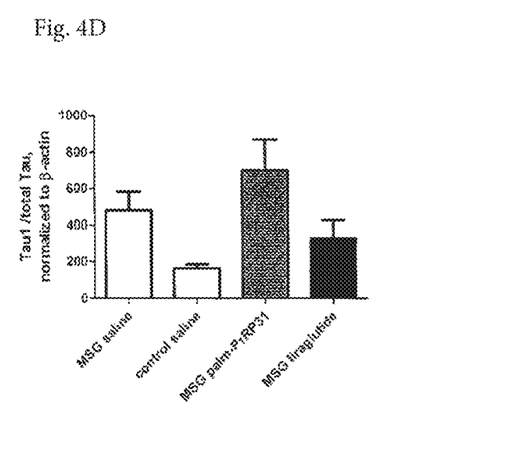

Tau Phosphorylation in Hippocampi of 6-Month-Old MSG Mice after 14-Day Treatment with Palmitoylated Analog or PrRP31 and Liraglutide Tau phosphorylation in hippocampi of 6 month-old-MSG mice after 14-day treatment was measured using WB analysis. In accordance with previous results, the increased phosphorylation of GSK-3β at Ser9 caused decreased phosphorylation of Tau protein at epitopes Ser396, Thr212 and Trh231 after 14-day-long treatment either with palmitoylated analog of PrRP31, or with liraglutide, as shown in FIGS. 4 A, B and C. Antibody Tau1, which recognizes not-hosphorylated Tau, did not show any significant differences among groups (FIG. 4D).

Phosphorylation of GSK-3β and Tau Protein at Epitope Thr231 in Hippocampi of 6-Month-Old MSG Mice after 14-Day-Long Treatment with Palmitoylated Analog of PrRP31 with Dichlorophenylalanin in Position 31

Figure 5A:
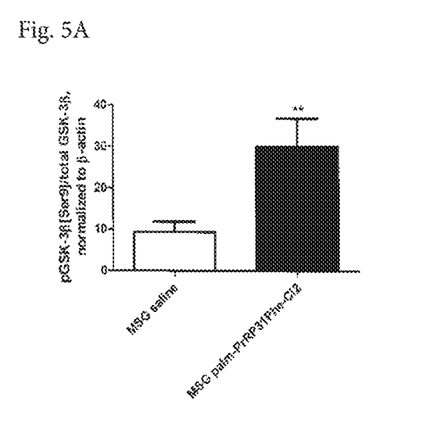
FIGS. 5A and 5B show phosphorylation of Tau protein at different Tau epitopes in hippocampi of 6-month-old MSG mice after 14-day treatment with palmitoylated PrRP31 with dichlorophenylalanin in position 31. Palmitoylated PrRP31 with dichlorophenylalanin in position 31 (5 mg/kg) was subcutaneously administered twice a day, in the morning and in the evening. Saline treated mice served as a control. Rate of phosphorylation was determined using WB. Data are mean±SEM, n=7-10 mice per group. Statistical analysis is 1-way ANOVA with Bonferroni post hoc test. Significance is * P<0.05 and *** P<0.001.
Figure 5B:
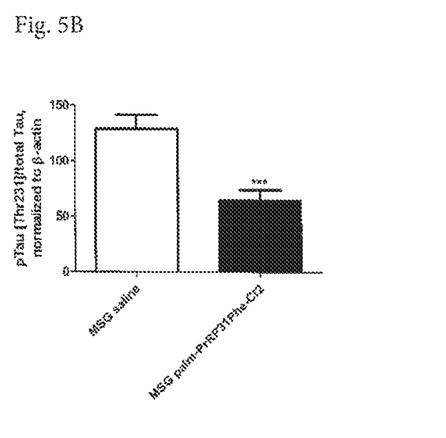

Phosphorylation was detected using the method of WB. As shown in FIGS. 5A and 5B, 14-day-long treatment with palmitoylated analog of PrRP31 with dichlorophenylalanin in position 31 increased phosphorylation of GSK-3β at Ser9 and subsequently led to a decreased phosphorylation of Tau protein at the epitope Thr231.

Figure 6:
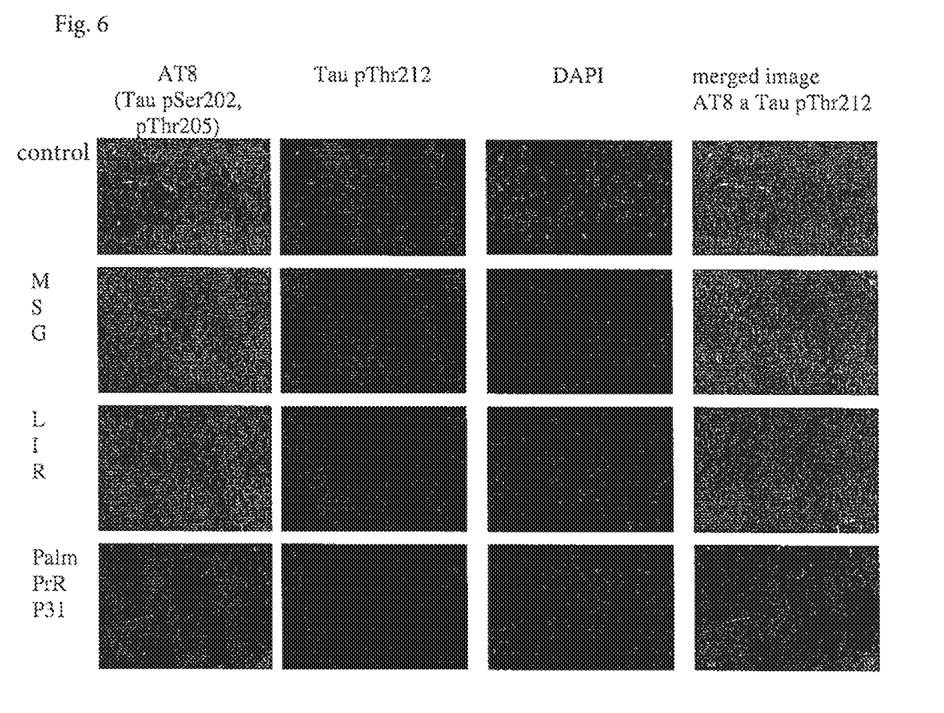
FIG. 6 shows immunohistochemical analysis of Tau hyperphosphorylation in CA1 region of the hippocampus of 6-month-old MSG mice and their age-matched controls and Tau hyperphosphorylation after 14-day treatment with liraglutide and palmitoylated PrRP31. Liraglutide (0.2 mg/kg) and palmitoylated human PrRP31 (5 mg/kg) were subcutaneously administered twice a day, in the morning and in the evening. Saline treated mice served as a control. Tau phosphorylation was determined using double immunohistochemical fluorescent staining.

Immunohistochemical Fluorescent Double Staining of Tau Phosphorylation in CA1 Region of Hippocampi of 6-Month-Old MSG Mice after 14-Day-Long Intervention with Palmitoylated Analog of PrRP31 and Liraglutide To evaluate the WB analysis the double immunohistochemical staining was used. As shown in FIG. 6, the phosphorylation of Tau protein at epitopes Thr212 and Ser202/Thr205 was increased in MSG mice at the age of 6 months compared to their age-matched control, both treated with saline. Increased phosphorylation is manifested by a stronger fluorescent signal using the laser of the same intensity.

After 14-day treatment with palmitoylated analog of PrRP31 and liraglutide, the Tau phosphorylation is decreased in hippocampal region CA1, which is manifested by a weaker fluorescent signal, using the laser of the same intensity.

Spatial Memory Testing in Thy-Tau 22 Mice Before and after the Treatment with LiPR31

Figure 7A:
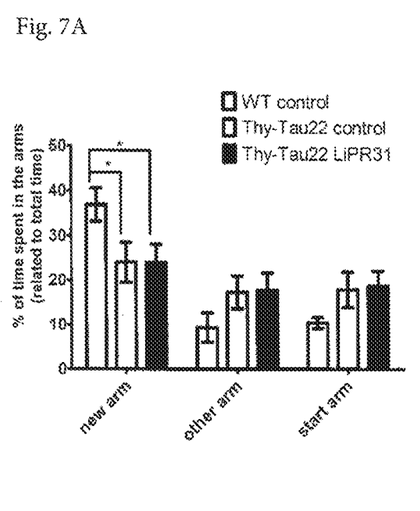
FIGS. 7A and 7B show spatial memory testing of Thy-Tau 22 mice and their WT controls in Ymaze. The memory was tested A/ before the beginning of the experiment and B/ after 2-month-long treatment with PrRP31 palmitoylated at $Lys^{11}$ through gamma glutamic acid linker (LiPR31) dissolved in PBS/5% Tween 80 using SC Alzet® osmotic pumps, the concentration was 5 mg/kg/day; PBS/5% Tween 80 was administered to the control group. Data are mean±SEM, n=10-12 animals per group. Statistical analysis is Student t-test. Significance is *P<0.05.
Figure 7B:
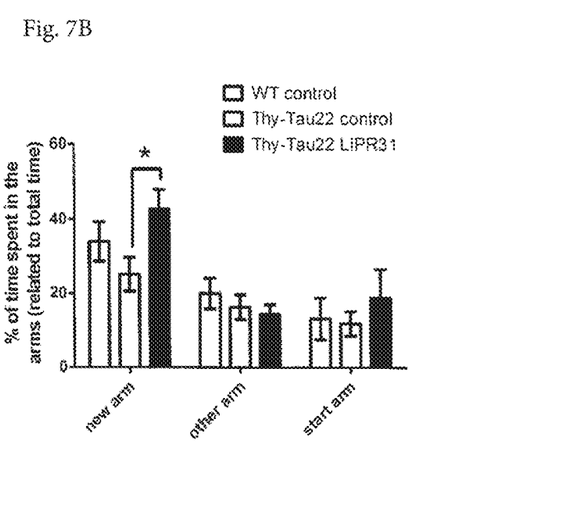

The spatial memory was tested before and after the treatment with LiPR31 in Thy-Tau22 mice and their age-matched WT control using the Y-maze; the WT and Thy-Tau22 control group was treated with PBS/5% Tween 80. As shown in FIG. 7A before the experiment the Thy-Tau22 mice spent significantly less time in the newly open arm, compared to WT animals. After the 2-month-long treatment with LiPR31 the Thy-Tau22 mice spent significantly more time in the new arm compared to the PBS/Tween 80 treated group, as shown in FIG. 7B.

Tau Phosphorylation in Hippocampi of 9-Month-Old Thy-Tau22 Mice after 2-Month-Long Treatment with LiPR31

Figure 8A:
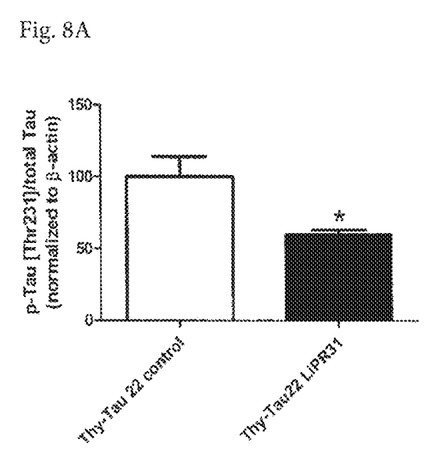
FIGS. 8A and 8B show Tau phosphorylation after 2-month-long treatment of Thy-Tau22 mice with LiPR31 dissolved in PBS/5% Tween 80 using SC Alzet® osmotic pumps, the concentration was 5 mg/kg/day; PBS/5% Tween 80 was administered to the control group. A/ phosphorylation on Tau epitope Thr231, B/ phosphorylation on Tau epitopes Ser396&Ser404 using AD2 antibody. Data are mean±SEM, n=7 10 animals per group. Statistical analysis is Student t-test. Significance is *P<0.05.
Figure 8B:
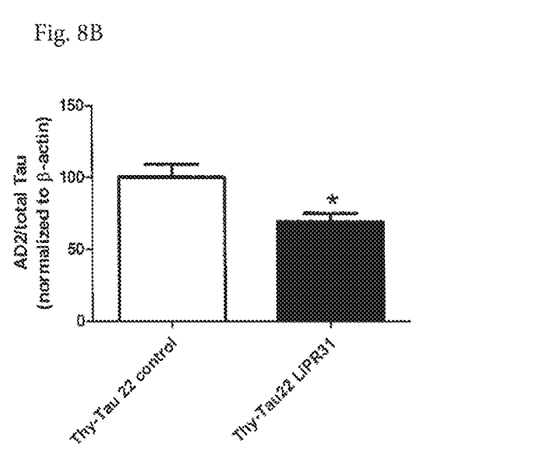

Tau phosphorylation was determined in the hippocampi of Thy-Tau22 mice treated with LiPR31 and their Thy-Tau22 control using the method of WB. Compared to the control group, the attenuation of Tau phosphorylation at epitopes Thr231, Ser396 5 and Ser404 was observed in hippocampi of Thy-Tau22 mice treated for 2 months with LiPR31, as shown in FIGS. 8A and 8B.

Survival of SH-SY5Y Cells after Treatment or after Pretreatment of LiPR31

The survival of SH-SY5Y cells, a cell line isolated from neuroblastoma bone marrow biopsy, which can be differentiated to mature human neurons, was determined after a methylglyoxal application, measured as their viability.

The SH-SY5Y (ATCC® CRL-2266™) cell line, obtained from LGC standards (Teddington, UK), was grown in DMEM medium supplemented with 10% heat-inactivated fetal bovine serum, 1% non-essential amino acids, 1% streptomycin/penicillin, and 2 mM L-glutamine at 37° C. in a humidified atmosphere containing 95% air/5% CO2. Medium was changed every 4-5 days, then cells were subcultured. For the assay, cells were cultured in 96-well plates at a density of $4 \times 10^4$ cells per well. Growth medium was exchanged for serum-free DMEM medium 16 h before an experiment.

In the pretreatment experiment, cells were pre-treated with $1 \times 10^{-7}$ mol·l$^{-1}$ hPrRP31 or LiPR31 or its analog No. 3 with a dicarboxylic fatty acid (dissolved in serum-free DMEM medium as vehicle) for 4 h (in octaplicates); then, methylglyoxal (MG) was added to a final concentration of 0.6 mmol·l$^{-1}$, and cells were incubated at 37° C. for 16 h.

In the treatment experiment, hPrRP31 or its analogs were added for 4 hours after 16 h incubation with MG. Other conditions were identical as in the pretreatment design.

Then, the MTT reagent dissolved in RPMI-1640 without phenol red was added to cells and cells were incubated for 4 h at 37° C. Living cells contain mitochondrial reductase that converts soluble MTT to insoluble formazan, which was subsequently dissolved in DMSO. The absorbance was measured at 560 nm.

Figure 9A:
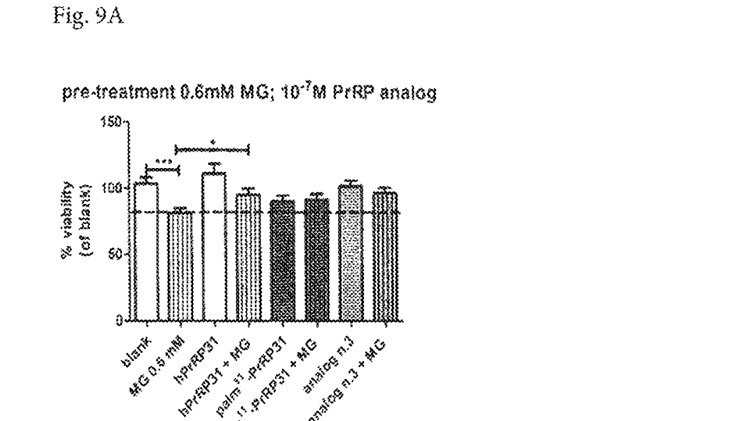
FIGS. 9A and 9B show the viability of SH-SY5Y cells in vitro, after treatment or after pretreatment of LiPR31. In the pretreatment experiment (see FIG. 9A), cells were pretreated with $1\times10^{-7}$ mol·$l^{-1}$ hPrRP31 or LiPR31 or its analog No. 3 with a dicarboxylic fatty acid (dissolved in serum-free DMEM medium as vehicle) for 4 h (in octaplicates); then, methylglyoxal (MG) was added to a final concentration of 0.6 mmol·$l^{-1}$, and cells were incubated at 37° C. for 16 h. In the treatment experiment (see FIG. 9B), hPrRP31 or or LiPR31 or its analog No. 3 were added for 4 hours after 16 h incubation with MG. Other conditions were identical as in the pretreatment design.
Figure 9B:
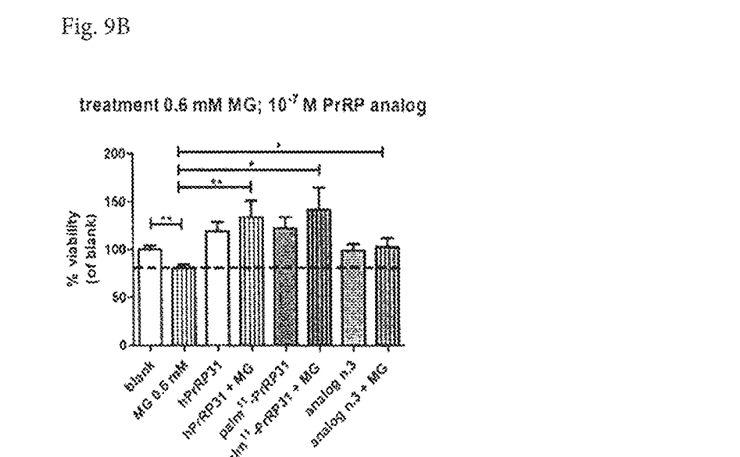

Tested LiPR31 as well as its analog acted on the cells neuroprotectively in vitro, preventing the apoptotic properties induced by toxic methylglyoxal (written as MG in FIGS.). Among the three comounds, palm$^{11}$-PrRP31 having the 16C fatty acid in the middle of the chain (LiPR31) provided better neuroprotective effect in comparison with non-lipidated human PrRP31 and also with analog No. 3 lipidated in the middle of the chain with a dicarboxylic fatty acid, as shown in FIGS. 9A and 9B.

APP/PS1 Mice

APP/PS1 mice are a widely used transgenic model of Alzheimer's disease-like Aβ pathology (McLean et al., 2011). These double transgenic mice express mutated amyloid precursor protein (APP) (Swedish mutation, K595N/M596L) and mutated presenilin (PS1) (deltaE9 PS1 exon deletion). Both mutations are associated with early-onset AD and accumulation of neurotoxic Aβ. Aβ deposition starts at 6 months of age with extensive accumulation in the hippocampus and cortex around 9 months (Jankowski et al., 2004). Astrocytosis and memory impairments appears at same time as plaque deposition (Kilgore et al., 2010).

APPswe/PSEN1dE9 (APP/PS1) male mice and their wild-type (WT) male controls (age 8 months), were obtained from Jackson Laboratory (Bar Harbor, Me., USA). Mice were subcutaneously injected once daily with saline or LiPR31 at dose 5 mg/kg for 2 months. Matrix solution of 1,5-diaminoanphthalene (10 mg/ml in 70% acetonitrile) was sprayed using iMatrixSpray (Tardo Gmbh, Switzerland). The experiments were performed using an UltrafleXtreme MALDI TOF/TOF (Bruker, Germany) in positive and negative mode.

Datasets were Evaluated Using Statistical Software SCiLS Lab 2016b (SCiLS GmbH, Germany) and ImageJ (NIH, Bethesda, USA).

Figure 10:
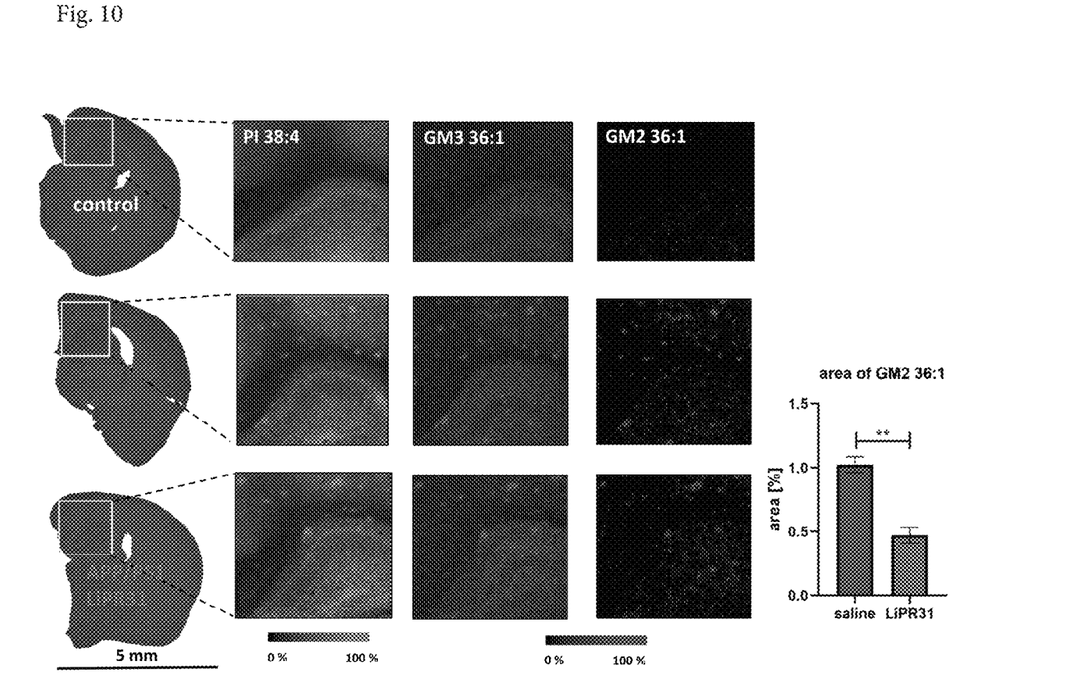
FIG. 10 shows MALDI MSI analysis in brains of wild-type (WT) control mice, APP/PS1 mice and APP/PS1 mice treated LiPR31. Optical images of the brain with phosphatidylinositol (PI 38:4, m/z 885.6), gangliosides (GM3 36:1, m/z 1179.6; GM2 36:1, m/z 1382.6) are shown in respective columns. Ion images were obtained in negative ion mode at spatial resolution 15 m. Statistical analysis is Student t-test. Significance is ** P<0.01. Data are mean±SEM, n=20 per group.

Distribution of various lipids in the area of pathological senile plaques in brains of APP/PS1 mice after 2-month-long treatment with LiPR31 In APP/PS1 mice a changed distribution of various lipids was observed in the area of pathological senile plaques compared to their controls. APP/PS1 mice showed higher concentration of gangliosides (GM2 36:1, GM3 36:1) and phosphatidyl inositols (PI 38:4, 36:4) compared to control mice (FIG. 10).

Visualization of GM2 36:1 was used for tracking of lipid changes because of its low concentration in the control mice. Two months of the treatment with LiPR31 reduced significantly area of lipids which were linked with senile plaques. The area of GM2 was decreased in the whole hippocampus and the cortex.

CONCLUSIONS

AD is characterized by two pathological changes in neurons: formation of non-soluble extracellular Aβ plaques and hyperphosphorylation of intracellular cytoskeletal Tau protein.

Within the framework of the present invention, the potential neuroprotective effect of tested compound was examined in the mouse model of obesity and insulin resistance, where obesity is caused by the application of monosodium glutamate (MSG) to newborn animals. Thy-Tau 22 mice, a model of AD like pathology, were also used to verify neuroprotective effect of tested compound.

Compounds increasing insulin sensitivity were tested regarding their effect on insulin signaling cascade and tau hyperphosphorylation in the brain (in hippocampus), in MSG obese mice before and after peptides application.

Compared to age-matched controls, the insulin resistance was observed in the brain of MSG obese mice. Decreased activation of insulin signaling cascade led to a decreased phosphorylation of GSK-3β at Ser9, which increased its kinase activity. GSK-3β is one of the most important kinases implicated in Tau phosphorylation. Consequently, hyperphosphorylation of Tau protein was observed at epitopes Ser396 and Thr231. After 14-day treatment with compounds increasing insulin sensitivity, which were palmitoylated analog of PrRP31, palmitoylated analog of PrRP31 with dichlorophenylalanin in position 31, and analog of GLP-1 liraglutide which served as a positive control, an enhanced activation of insulin signaling cascade, including increased phosphorylation of GSK-3β at Ser9, and decreased phosphorylation of Tau protein at epitopes Ser396, Thr212 and Thr231 was observed.

Tested analogs of palmitoylated PrRP enhanced insulin signaling cascade in the hippocampi of 6-month-old insulin resistant MSG mice after 14-day SC treatment. Attenuated Tau phosphorylation was also observed; Tau hyperphosphorylation is the pathological change found in brains of AD patients.

PrRPs lipidated in the middle of the chain affect the survival of SH-SY5Y cells. Thus, the compounds of the invention exhibit neuroprotective biological activity in their own right, in an environment where BBB does not apply. Their protective effect, therefore, can't be attributed to facilitated passage through BBB, although it is indispensable that the drugs intended for action in the brain tissue pass through such a barrier.

LiPR31 also significantly reduced completely different markers of Alzheimer's disease-like pathology, mutated amyloid precursor protein (APP) (Swedish mutation, K595N/M596L) and mutated presenilin (PS1) (deltaE9 PS1 exon deletion). Two months of the treatment with LiPR31 changed distribution of various lipids observed in an area of pathological senile plaques and reduced significantly the area of lipids linked with senile plaques. The area of GM2 was decreased in the whole hippocampus and the cortex.

INDUSTRIAL APPLICABILITY

New analogs of prolactin releasing peptide (PrRP) represent neuroprotective agents for peripheral treatment and prevention of diseases, which are Alzheimer's disease (AD), Parkinson's disease (PD), cognitive impairment no dementia (CIND) and brain trauma.

REFERENCES

Belarbi K, Burnouf S, Fernandez-Gomez F J, Laurent C, Lestavel S, Figeac M, Sultan A, Troquier L, Leboucher A, Caillierez R, Grosjean M E, Demeyer D, Obriot H, Brion I, Barbot B, Galas M C, Staels B, Humez S, Sergeant N, Schraen-Maschke S, Muhr-Tailleux A, Hamdane M, Buee L and Blum D (2011), *Neurobiol Dis* 43:486-494.

Elefteriou F, Takeda S, Liu X, Armstrong D and Karsenty G (2003), *Endocrinology* 144:3842-3847.

Hinuma S, Habata Y, Fujii R, Kawamata Y, Hosoya M, Fukusumi S, Kitada C, Masuo Y, Asano T, Matsumoto H, Sekiguchi M, Kurokawa T, Nishimura O, Onda H and Fujino M (1998), *Nature* 393:272-276.

Jankowski J L, Fadale D J, Anderson J, Xu G M, Gonzales v, Jenkins N A, Copeland N G, Lee M K, Younkin L H, Wagner S L, Younkin S G, Borchelt D R (2004), *Human Molecular Genetics* 13(2):159-170.

Kilgore M, Miller C A, Fass D M, Hennig K M, Haggarty S J, Sweatt J D, Rumbaugh G (2010), *Neuropsychopharmacology* 35(4):870-80.

Maletínská L, Maixnerová J, Matyskovi R, Haugvicová R, Sloncová E, Elbert T, Slaninová J, elezná B (2007), *Eur J Pharmacol* 559:109-114.

Maletínská L, Toma R S, Pirnik Z, Kiss A, Slaninová J, Haluzík M and elezná B (2006), *Regul Pept* 136:58-63.

McClean P L, Parthsarathy V, Faivre E, Holscher C (2011), *J. Neurosci.*, 31:6587-6594.

Nagelová V, Pirnik Z, elezná B a Maletínská L (2014), *Brain Res* 1547:16-24.

Olney J W (1969), *Science* 164:719-721.

Schindowski K, Bretteville A, Leroy K, Begard S, Brion J P, Hamdane M and Buee L (2006), *Am J Pathol* 169:599-616.

Van der Jeugd A, Ahmed T, Burnouf S, Belarbi K, Hamdame M, Grosjean M E, Humez S, Balschun D, Blum D, Buee L and D'Hooge R (2011), *Neurobiology of learning and memory* 95:296-304.

Violet M, Delattre L, Tardivel M, Sultan A, Chauderlier A, Caillierez R, Talahari S, Nesslany F, Lefebvre B, Bonnefoy E, Buee L a Galas M C (2014), *Frontiers in cellular neuroscience* 8:84.

Vorhees C V a Williams M T (2006), *Nature protocols* 1:848-858.

---

The invention claimed is:

1. A method of treatment of neurodegenerative diseases selected from Alzheimer's disease (AD), comprising the step of administering at least one lipidated neuropeptide to a subject in need thereof, the at least one lipidated neuropeptide being a lipidated neuropeptide based on prolactin-releasing peptide, selected from (SEQ ID NO. 6)
(N-palm)SRTHRHSMEIRTPDINPAWYASRGIRPVGRF-NH$_2$ (5), and (SEQ ID NO. 10)
SRTHRHSMEIKTPDINPAWYASRGIRPVGRF-NH$_2$ (9),
|
X$^2$(palm)

wherein palm is hexadecanoic acid and X$^2$ is γ-glutamic acid.

* * * * *